United States Patent
Higashi et al.

(10) Patent No.: US 12,319,749 B2
(45) Date of Patent: Jun. 3, 2025

(54) ANTIBODY AND FUNCTIONAL FRAGMENT THEREOF

(71) Applicant: Sumitomo Chemical Company, Limited, Tokyo (JP)

(72) Inventors: Kiyoshi Higashi, Osaka (JP); Koichi Saito, Osaka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 964 days.

(21) Appl. No.: 17/427,545

(22) PCT Filed: Jan. 31, 2020

(86) PCT No.: PCT/JP2020/003782
§ 371 (c)(1),
(2) Date: Jul. 30, 2021

(87) PCT Pub. No.: WO2020/158943
PCT Pub. Date: Aug. 6, 2020

(65) Prior Publication Data
US 2022/0119548 A1    Apr. 21, 2022

(30) Foreign Application Priority Data
Feb. 1, 2019 (JP) .................. 2019-017285

(51) Int. Cl.
| | | |
|---|---|---|
| C07K 16/32 | (2006.01) | |
| A61K 39/00 | (2006.01) | |
| A61K 51/10 | (2006.01) | |
| A61P 35/00 | (2006.01) | |
| G01N 33/574 | (2006.01) | |

(52) U.S. Cl.
CPC .......... *C07K 16/32* (2013.01); *A61K 51/1045* (2013.01); *A61P 35/00* (2018.01); *G01N 33/57492* (2013.01); *A61K 2039/505* (2013.01)

(58) Field of Classification Search
None
See application file for complete search history.

(56) References Cited

U.S. PATENT DOCUMENTS

| | | |
|---|---|---|
| 5,227,160 A | 7/1993 | Nudelman et al. |
| 2012/0082667 A1 | 4/2012 | Yokoseki et al. |
| 2016/0068611 A1 | 3/2016 | Okuda |
| 2016/0136299 A1 | 5/2016 | Avila et al. |
| 2018/0320136 A1 | 11/2018 | Magnani |
| 2019/0060481 A1 | 2/2019 | Avila et al. |
| 2019/0353659 A1 | 11/2019 | Higashi et al. |
| 2022/0088214 A1 | 3/2022 | Avila et al. |

FOREIGN PATENT DOCUMENTS

| | | | |
|---|---|---|---|
| CN | 102459335 A | 5/2012 | |
| CN | 104418950 A | 3/2015 | |
| CN | 108025083 A | 5/2018 | |
| WO | WO-99/15628 A1 | 4/1999 | |
| WO | WO-2017/079215 A1 | 5/2017 | |
| WO | WO-2018143336 A1 * | 8/2018 | ......... G01N 33/5436 |

OTHER PUBLICATIONS

Janeway et al., Immunology Third Edition, Garland Publishing Inc. 1997, Chapter 3, Structure of the Antibody Molecule and Immunoglobulin Genes, pp. 3:1-3:11 (Year: 1997).*
Gerdes et al. Emerging understanding of multiscale tumor heterogeneity, Front. Oncol. Dec. 18, 2014 doi: 10.3389/fonc.2014.00366, pp. 1-12 (Year: 2014).*
Higashi et al., Carbohydrate 3'-sialyllactose as a novel target for theranostics in pancreatic ductal adenocarcinoma, Tumor Biology, Oct. 2020: 1-9, Publication Date: Oct. 2020 (Year: 2020).*
Gura, T., Systems for Identifying New Drugs Are Often Faulty, Science, 1997, 278:1041-1042 (Year: 1997).*
Kaiser, J., First pass at cancer genoome reveals complex landscape, Science, 2006, 313:1370 (Year: 2006).*
Sawada et al., Human Monoclonal Antibodies to Sialyl-Lewisa (CA19.9) with Potent CDC, ADCC, and Antitumor Activity, Clin Cancer Res, 17(5), 1024-1032, Publication Date: Mar. 1, 2011 (Year: 2011).*
Extended European Search Report issued in connection with EP Appl. Ser. No. 20748501.2 dated Sep. 9, 2022.
Higashi Kiyoshi et al., "Carbohydrate 3'-sialyllactose as a novel target for theranostics in pancreatic ductal adenocarcinoma", Tumor Biology, vol. 42, No. 10, Oct. 8, 2020.
Smith D.F. et al., "Antibodies against sialyloligosaccharides coupled to protein.", Journal of Biological Chemistry, vol. 255, No. 1, Jan. 10, 1980, pp. 55-59.
Office Action issued in corresponding Chinese Patent Application No. 202080017723.6 dated Mar. 29, 2024 (10 pages).
Ding, Kai, et al., "Monoclonal antibody against a lactose epitope of glycosphingolipids binds to melanoma tumour cells", Glycoconjugate Journal, 1993, vol. 10, pp. 395-405.
International Search Report dated Mar. 10, 2020 issued in International Application No. PCT/JP2020/003782, with English translation, 6 pages.
Wu, Erxi, et al., "CA 19-9 and Pancreatic Cancer", Clin Adv Hematol Oncol. Author manuscript; available in PMC Apr. 23, 2013, 5 pages.

(Continued)

*Primary Examiner* — Peter J Reddig
*Assistant Examiner* — Cheng Lu
(74) *Attorney, Agent, or Firm* — Foley & Lardner LLP

(57) ABSTRACT

Disclosed are an antibody or a functional fragment thereof binding to 3'-sialyl lactose and comprising a heavy chain variable region which is optionally substituted with 3 or less amino acids and which comprises a CDR sequence consisting of an amino acid sequence ARKNGGLDYAMDY (SEQ ID NO: 3), a polynucleotide encoding the antibody or the functional fragment thereof, an expression vector comprising the polynucleotide, and a test drug for a disease and a pharmaceutical composition comprising the antibody or the functional fragment thereof.

17 Claims, 4 Drawing Sheets
Specification includes a Sequence Listing.

(56) References Cited

OTHER PUBLICATIONS

Zhejiang, "Clinical significance of serum sialic acid test in the diagnosis of pancreatic cancer", JITCWM, vol. 14, No. 7, 2004, pp. 419-420.

* cited by examiner

ANTIBODY AND FUNCTIONAL FRAGMENT THEREOF

CROSS-REFERENCE TO RELATED APPLICATIONS

The present application is a 371 of International Application No. PCT/JP2020/003782, filed Jan. 31, 2020, which is based upon and claims the benefit of priority from Japanese Patent Application No. 2019-017285, filed Feb. 1, 2019, the contents of each of which are incorporated herein by reference in their entirety.

SEQUENCE LISTING

The instant application contains a Sequence Listing which has been submitted electronically in ASCII format and is hereby incorporated by reference in its entirely. Said ASCII copy, created on Jul. 30, 2021, is named P19-296-SE-QUENCE-LISTING.txt and is 5,306 bytes in size.

TECHNICAL FIELD

The present invention relates to an antibody and a functional fragment thereof. Furthermore, the present invention relates to a polynucleotide encoding the antibody or the functional fragment thereof, an expression vector containing the polynucleotide, and a test drug for a disease and a pharmaceutical composition containing the antibody or the functional fragment thereof.

BACKGROUND ART

Cancer is the leading cause of death in Japan, and the number of deaths from cancer is increasing year by year as the average life expectancy increases. Early diagnosis is considered to be most important for reducing the number of deaths from cancer. However, in many cases, there are no characteristic symptoms in the early stages, and at the time when a cancer is diagnosed, the cancer has already progressed and treatment becomes difficult. In addition, cancers such as pancreatic cancer, even if the cancer tissue can be excised by surgery, the recurrence rate after surgery is high, and postoperative monitoring is indispensable. Therefore, a simple cancer test method such as a blood test plays an important role since a reliable effect can be obtained by proper implementation.

So far, many antibodies against cancer antigens have been produced, and in particular, monoclonal antibodies are generally used since monoclonal antibodies have high sensitivity and specificity and can be used semi-permanently. For pancreatic cancer, which is the most difficult to diagnose early, a test method using CA19-9 monoclonal antibody has been reported (Non-patent Literature 1). In addition, in a cancer test, CEA antibody is used for gastric cancer, and CA125 antibody is used for ovarian cancer.

CITATION LIST

Non-Patent Literature

NPL 1: Erxi W. Shuang Z. Kruttika B. Qingyong M.: CA19-9 and pancreatic cancer. Clin Adv Hematol Oncol. 2013 11(1): 53-55.

SUMMARY OF INVENTION

Technical Problem

An object of the present invention is to provide an antibody or a functional fragment thereof that can be used for testing and treating a cancer. Furthermore, an object of the present invention is to provide a polynucleotide encoding the antibody or the functional fragment thereof, an expression vector containing the polynucleotide, and a test drug for a disease and a pharmaceutical composition containing the antibody or the functional fragment thereof.

Solution to Problem

The present inventors have conducted thorough research in order to achieve the above objects, and as a result, the present inventors have obtained an antibody by immunizing a mouse with human ES cells, and have found that the possibility of having developed a cancer can be determined by using an antigen value of the antibody as an index. Furthermore, the present inventors also have found that the antibody has cancer cytotoxic activity.

The present invention has been completed through further research based on these findings, and provides the following antibody or functional fragment thereof, polynucleotide, expression vector, test drug for a disease, and pharmaceutical composition.

Item 1. An antibody or a functional fragment thereof binding to 3'-sialyl lactose and comprising a heavy chain variable region which is optionally substituted with 3 or less amino acids and which comprises a CDR sequence consisting of an amino acid sequence ARKNGGLDYAMDY (SEQ ID NO: 3).

Item 2. An antibody or a functional fragment thereof binding to 3'-sialyl lactose and comprising:
(i) a heavy chain variable region which is optionally substituted with 3 or less amino acids and which comprises a CDR sequence consisting of an amino acid sequence GIDFSIYW (SEQ ID NO: 1), a CDR sequence consisting of an amino acid sequence INSDSSTI (SEQ ID NO: 2), and a CDR sequence consisting of an amino acid sequence ARKNG-GLDYAMDY (SEQ ID NO: 3), and/or
(ii) a light chain variable region which is optionally substituted with 1 or less amino acids and which comprises a CDR sequence consisting of an amino acid sequence KSISKY (SEQ ID NO: 4), a CDR sequence consisting of an amino acid sequence of SGS, and a CDR sequence consisting of an amino acid sequence of QQHNEYPWT (SEQ ID NO: 5).

Item 3. The antibody or the functional fragment thereof according to item 1 or 2, wherein the antibody is derived from a vertebrate.

Item 4. The antibody or the functional fragment thereof according to any one of items 1 to 3, wherein the antibody is derived from a mouse.

Item 5. The antibody or the functional fragment thereof according to any one of items 1 to 4, wherein the antibody is IgG or IgM.

Item 6. The antibody or the functional fragment thereof according to any one of items 1 to 5, wherein the functional fragment is Fab, Fab', F(ab')$_2$, scFv, a diabody, a triabody, a tetrabody, or a minibody.

Item 7. A polynucleotide encoding the antibody or the functional fragment thereof according to any one of items 1 to 6.

Item 8. An expression vector comprising the polynucleotide according to item 7.

Item 9. A test drug for a disease, comprising the antibody or the functional fragment thereof according to any one of items 1 to 6.

Item 10. The test drug according to item 9, wherein the disease is a cancer.

Item 11. The test drug according to item 10, wherein the cancer is at least one cancer selected from the group consisting of pancreatic cancer, melanoma, thyroid cancer, gastric cancer, testicular cancer, and ovarian cancer.

Item 12. A pharmaceutical composition for diagnosing a disease, comprising the antibody or the functional fragment thereof according to any one of items 1 to 6 labeled with a diagnostic agent.

Item 13. The pharmaceutical composition according to item 12, wherein the diagnostic agent is a radioactive substance.

Item 14. A pharmaceutical composition for treating a disease, comprising the antibody or the functional fragment thereof according to any one of items 1 to 6.

Item 15. A pharmaceutical composition for treating a disease, comprising the antibody or the functional fragment thereof according to any one of items 1 to 6 labeled with a therapeutic agent.

Item 16. The pharmaceutical composition according to item 15, wherein the therapeutic agent is an anticancer agent.

Item 17. The pharmaceutical composition according to item 15, wherein the therapeutic agent is a radioactive substance.

The present invention also provides the following.

Item 18. A method for testing a possibility of having developed a cancer such as pancreatic cancer, the method comprising (1) a step of measuring an amount or a concentration of an antigen in a biological sample collected from a subject, using the test drug according to any one of items 9 to 11.

Item 19. The method according to item 18, further comprising (2) a step of determining that the possibility of having developed a cancer such as pancreatic cancer in the subject is high, when a value of the amount or the concentration of the antigen measured in the step (1) is equal to or higher than a preset cutoff value.

Item 20. A method for diagnosing a cancer such as pancreatic cancer in a subject, the method comprising:
(1a) a step of measuring an amount or a concentration of an antigen in a biological sample collected from the subject, using the test drug according to any one of items 9 to 11; and
(2a) a step of determining that the possibility of having developed a cancer such as pancreatic cancer in the subject is high, when a value of the amount or the concentration of the antigen measured in the step (1a) is equal to or higher than a preset cutoff value.

Item 21. The method according to item 20, further comprising (3) a step of applying a diagnostic method for a cancer such as pancreatic cancer to the subject for which the possibility of having developed a cancer such as pancreatic cancer is determined to be high in the step (2a).

Item 22. The method according to item 21, wherein the diagnostic method for a cancer such as pancreatic cancer applied in the step (3) is at least one method selected from the group consisting of a biopsy method, a PET test method, a CT test method, and an ultrasonic test method.

Item 23. A method for testing and treating a cancer such as pancreatic cancer in a subject, the method comprising:

(1b) a step of measuring an amount or a concentration of an antigen in a biological sample collected from the subject, using the test drug according to any one of items 9 to 11;
(2b) a step of determining that the possibility of having developed a cancer such as pancreatic cancer in the subject is high, when a value of the amount or the concentration of the antigen measured in the step (1b) is equal to or higher than a preset cutoff value;
(3b) a step of applying a diagnostic method for a cancer such as pancreatic cancer to the subject for which the possibility of having developed a cancer such as pancreatic cancer is determined to be high in the step (2b); and
(4b) a step of performing treatment for a cancer such as pancreatic cancer on a subject for which the possibility of having developed a cancer such as pancreatic cancer is determined to be high in the step (2b) or a subject determined to have a cancer such as pancreatic cancer in the step (3b).

Item 24. A method for diagnosing a cancer such as pancreatic cancer in a subject, the method comprising a step of administering the antibody or the functional fragment thereof according to any one of items 1 to 6 labeled with a diagnostic agent, to a subject in need of the diagnosis.

Item 25. The method according to item 24, wherein the diagnostic agent is a radioactive substance.

Item 26. A method for treating a cancer such as pancreatic cancer in a subject, comprising a step of administering the antibody or the functional fragment thereof according to any one of items 1 to 6 to a subject in need of the treatment.

Item 27. The method according to item 26, wherein the antibody or the functional fragment thereof is labeled with a therapeutic agent.

Item 28. The method according to item 27, wherein the therapeutic agent is an anticancer agent.

Item 29. The method according to item 27, wherein the therapeutic agent is a radioactive substance.

Advantageous Effects of Invention

According to the present invention, it is possible to provide an antibody or a functional fragment thereof that can be used for diagnosing and treating a cancer. In addition, when a test drug containing the antibody or the functional fragment thereof is used, it is possible to test the possibility of having developed a cancer such as pancreatic cancer. Furthermore, when a pharmaceutical composition containing the antibody or the functional fragment thereof is used, it is possible to diagnose and treat a cancer such as pancreatic cancer.

DESCRIPTION OF EMBODIMENTS

Figure 1:
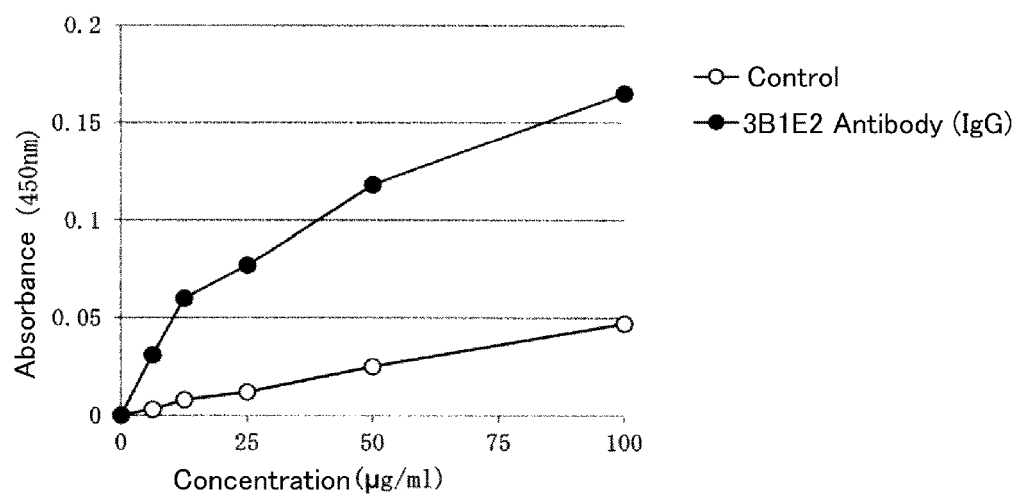
FIG. 1 shows the results of binding of a 3B1E2 antibody (mouse IgG2a) and 3'-sialyl lactose performed in Example 2, in which the vertical axis represents absorbance at 450 nm and the horizontal axis represents the concentration of the antibody.

Hereinafter, embodiments of the present invention will be described in detail.

It should be noted that, in the present specification, "comprise" also includes the meaning of "essentially consist of" and the meaning of "consist of".

1. Antibody or Functional Fragment Thereof

An example of a specific antigen to which the antibody or the functional fragment thereof of the present invention can bind is 3'-sialyl lactose. An example of the structural formula of 3'-sialyl lactose is the following formula (A) [wherein, Ac represents an acetyl group], the molecular formula thereof is $C_{23}H_{34}NO_{19}$, and the molecular weight thereof is 628.51.

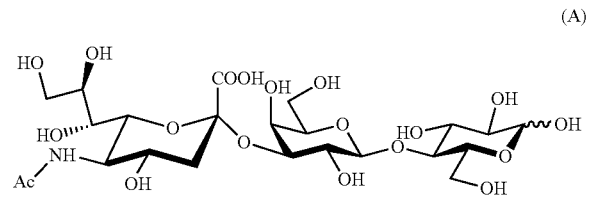

(A)

The 3'-sialyl lactose sugar chain is a sugar chain represented by Neu5Acα(2→3)Galβ(1→4)Glc, that is, a sugar chain in which the hydroxy group at the 2-position of neuromic acid (Neu5Ac) and the hydroxy group at the 3-position of galactose (Gal) are linked by an α-glycosidic bond, and the hydroxy group at the 1-position of galactose (Gal) and the hydroxy group at the 4-position of glucose (Glc) are linked by a β-glycosidic bond.

The antibody or the functional fragment thereof of the present invention is characterized by comprising a heavy chain variable region which is optionally substituted with 3 or less amino acids and which comprises a CDR sequence consisting of an amino acid sequence ARKNG-GLDYAMDY (SEQ ID NO: 3).

The antibody or the functional fragment thereof of the present invention is also characterized by comprising
  (i) a heavy chain variable region which is optionally substituted with 3 or less amino acids and which comprises a CDR sequence consisting of an amino acid sequence GIDFSIYW (SEQ ID NO: 1), a CDR sequence consisting of an amino acid sequence INSDSSTI (SEQ ID NO: 2), and a CDR sequence consisting of an amino acid sequence ARKNG-GLDYAMDY (SEQ ID NO: 3), and/or
  (ii) a light chain variable region which is optionally substituted with 1 or less amino acids and which comprises a CDR sequence consisting of an amino acid sequence KSISKY (SEQ ID NO: 4), a CDR sequence consisting of an amino acid sequence SGS, and a CDR sequence consisting of an amino acid sequence QQH-NEYPWT (SEQ ID NO: 5).

Amino acid substitutions are performed such that binding ability to 3'-sialyl lactose is maintained. The above "optionally substituted with 3 or less amino acids" and "optionally substituted with 1 or less amino acids" mean that a total of 3 or less, or 1 or less amino acids are substituted in the heavy chain variable region or the light chain variable region, and amino acid substitutions are preferably performed in the CDR part.

The number of amino acid substitutions is preferably 2 or less, more preferably 1 or less, and further preferably 0. When substituting an amino acid, it is considered that the activity of the original antibody fragment can be easily maintained by substitution with an amino acid having similar properties. Techniques for substituting an amino acid in a particular amino acid sequence are known.

The "functional fragment thereof" is defined as a part of an antibody comprising a heavy chain polypeptide and/or light chain polypeptide having part or all of the binding activity as the antibody from which the functional fragment is derived. Examples of the functional fragment include Fd, Fv, Fab, F(ab'), F(ab)$_2$, F(ab')$_2$, single chain Fv (scFv), a diabody, a triabody, a tetrabody, and a minibody.

The "heavy chain" means a polypeptide chain of about 50 to 70 kDa in which an amino-terminal portion includes a variable region of about 120 to 130 or more amino acids and a carboxy-terminal portion includes a constant region. The constant region can be one of five different types called alpha (α), delta (δ), epsilon (ε), gamma (γ), and mu (μ), based on the amino acid sequence of the heavy chain constant region. The different types of heavy chains differ in size, α, δ, and γ contain approximately 450 amino acids, and μ and ε contain approximately 550 amino acids. When these different types of heavy chains are combined with light chains, five well-known classes of antibodies, IgA, IgD, IgE, IgG, and IgM, including four subclasses of IgG (IgG1, IgG2, IgG3, and IgG4), are produced.

The "light chain" means a polypeptide chain of about 25 kDa in which an amino-terminal portion includes a variable region of about 100 to about 110 or more amino acids and a carboxy-terminal portion includes a constant region. The approximate length of the light chain is 211 to 217 amino acids. There are two different types called kappa (κ) or lambda (λ) based on the amino acid sequence of the constant domain.

The "variable region" is generally located at the amino terminus of a light or heavy chain, contains approximately 120 to 130 residues in the heavy chain, contains approximately 100 to 110 residues in the light chain, and is a part of the light chain or heavy chain of an antibody that is involved in binding and specificity to a particular antigen. The variable region has a wide range of sequences different among different antibodies, the variability of the sequence is concentrated in the CDR (complementarity determining region) existing in the variable region, and the low-variability part in the variable region is referred to as a framework region. The CDRs of the light chain and the heavy chain are mainly involved in the interactions between antibodies and antigens.

The "CDR" means one of the three hypervariable regions (H1, H2, or H3) within the non-framework region of an antibody heavy chain (H) variable region β-sheet framework, or one of the three hypervariable regions (L1, L2, or L3) within the non-framework region of an antibody light chain (L) variable region β-sheet framework. The CDRs are hypervariable region sequences scattered within a framework region sequence.

The "binding" means an interaction between molecules in which a complex is formed. Interactions are, for example, non-covalent interactions including hydrogen bonds, ionic bonds, hydrophobic interactions, and/or van der Waals interactions. Binding of the antibody or the functional fragment thereof can be detected using, for example, an enzyme binding immunoadsorption assay, which is a method presented in Examples 2 and 4, or other known methods.

The antibody of the present invention is preferably derived from a vertebrate such as a mouse, rat, cow, rabbit, goat, sheep, and guinea pig, and more preferably derived from a mouse.

The isotype of the antibody of the present invention is not particularly limited. Examples of the isotype include IgG (IgG1, IgG2, IgG3, IgG4), IgA, IgD, IgE, IgG, and IgM. Among them, IgG or IgM is preferable.

Preferably, the CDR amino acid sequences of SEQ ID NO: 1 to 3 correspond to heavy chain variable regions CDR1 to 3, respectively, and the CDR amino acid sequences of SEQ ID NO: 4, SGS, and SEQ ID NO: 5 correspond to light chain variable regions CDR1 to 3, respectively.

The antibody of the present invention preferably comprises both the heavy chain variable region and the light chain variable region.

The polynucleotide of the present invention is characterized by encoding the antibody or the functional fragment thereof.

The "polynucleotide" means a nucleotide in the form of a polymer of any length that is either deoxyribonucleotide or ribonucleotide or an analog thereof. The sequence of the polynucleotide consists of four types of nucleotide bases: adenine (A); cytosine (C); guanine (G); thymine (T); and uracil (U) instead of thymine when the polynucleotide is an RNA. Examples of the polynucleotide can include genes, gene fragments, exons, introns, messenger RNAs (mRNAs), transfer RNAs, ribosomal RNAs, ribozymes, cDNAs, recombinant polynucleotides, and the like. The polynucleotide means both double-stranded and single-stranded molecules.

The nucleotide sequences encoding the CDR amino acid sequences of SEQ ID NO: 1 to 3 are, for example, GGAATCGATTTTAGTATATACTGG (SEQ ID NO: 6), ATTAATTCAGATAGCAGTACAATA (SEQ ID NO: 7), and GCAAGAAAGAATGGGGGATTGGACTATGC-TATGGACTAC (SEQ ID NO: 8), respectively. In addition, the nucleotide sequences encoding the CDR amino acid sequences of SEQ ID NO: 4, SGS, SEQ ID NO: 5 are, for example, AAGAGCATTAGCAAATAT (SEQ ID NO: 9), TCTGGATCC, and CAACAGCATAAT-GAATACCCGTGGACG (SEQ ID NO: 10), respectively.

The polynucleotide of the present invention can be chemically synthesized, or can also be obtained by PCR amplification using synthetic primers that can hybridize to the 3' and 5' ends of a sequence, or by cloning using oligonucleotide probes specific for a particular nucleic acid sequence, from a suitable source (for example, cDNA isolated from antibody-expressing cells, such as hybridoma cells, selected to express an antibody). The amplified nucleic acid produced by PCR can then be cloned into a replicable cloning vector using any method well known in the art.

When the polynucleotide encoding the antibody or the functional fragment thereof of the present invention is obtained, a vector for producing the antibody or the functional fragment thereof can be produced by recombinant DNA technology using a method well known in the art, and an expression vector containing the coding sequence of the antibody or the functional fragment thereof and appropriate transcription and translation control signals can be further constructed using a well-known method. In addition, although the constant region differs greatly between species such as human, mouse, and rat, the constant regions of antibodies of the same species are very similar. Thus, antibodies of human, mouse, rat, and the like can be produced by cloning into a vector containing a nucleotide sequence encoding the constant region of each species.

The expression vector can be introduced into host cells by a conventional method, and then the transfected cells can be cultured by a conventional method to produce the antibody or the functional fragment thereof of the present invention. In order to express the entirety of an immunoglobulin molecule, a vector encoding both a heavy chain and a light chain may be co-expressed in host cells.

Various host-expression vector systems can be utilized to express the antibody or the functional fragment thereof of the present invention. Examples of host-expression vector systems include microorganisms such as bacteria (for example, *Escherichia coli*, *Bacillus subtilis*) transformed with a recombinant bacteriophage DNA, plasmid DNA, or cosmid DNA expression vector containing the antibody coding sequence, and yeast (for example, *Saccharomyces pikia*) transformed with a recombinant yeast expression vector containing the antibody coding sequence, insect cells infected with a recombinant virus expression vector (for example, baculovirus) containing the antibody coding sequence, plant cells infected with a recombinant virus expression vector (for example, cauliflower mosaic virus, TMV) or transformed with a recombinant plasmid expression vector (for example, Ti plasmid) containing the antibody coding sequence, and mammalian cells (for example, COS, CHO, HEK293, 3T3 cells) having a recombinant expression construct containing a promoter derived from the genome of mammalian cells (for example, metallothionein promoter) or a promoter derived from a mammalian virus (for example, late adenovirus promoter).

When the antibody or the functional fragment thereof of the present invention is produced by recombinant expression, the antibody or the functional fragment thereof can be purified by a method known in the art for purifying immunoglobulin molecules, for example, chromatography (for example, ion exchange chromatography, Protein A chromatography, gel filtration column chromatography), centrifugation, salting out, etc. Furthermore, the antibody or the functional fragment thereof of the present invention can be fused with a known heterologous polypeptide sequence in order to facilitate purification. For example, the antibody or the functional fragment thereof of the present invention can be purified by recombinantly adding a poly-histidine tag (His tag), FLAG tag, hemagglutinin tag (HA tag), or myc tag.

Moreover, the functional fragment of the antibody of the present invention can be produced by a known method. For example, the Fab and F(ab')$_2$ fragments of the antibody of the present invention can be produced by proteolytic cleavage of an immunoglobulin molecule using an enzyme such as papain (to produce the Fab fragment) and pepsin (to produce the F(ab')$_2$ fragment).

2. Test Drug for Disease

The test drug for a disease of the present invention is characterized by comprising the antibody or the functional fragment thereof. The test drug of the present invention is particularly a drug for testing the possibility of having developed a cancer.

The test drug for a disease of the present invention can be used for a method for testing (or determining) the possibility of having developed a cancer such as pancreatic cancer, which comprises a step of measuring the amount or concentration of an antigen that binds to the antibody or the functional fragment thereof of the present invention, in a biological sample collected from a subject (in the present specification, the method is sometimes referred to as "a test method of the present invention"). This will be described below.

The cancers to be tested, such as pancreatic cancer, are not particularly limited and include cancers of all types, stages, and the like. The types of cancers are preferably pancreatic cancer, melanoma, thyroid cancer, gastric cancer, testicular cancer, and ovarian cancer, and particularly preferably pancreatic cancer. Examples of the types of pancreatic cancer include pancreatic ductal cancer, pancreatic endocrine tumor, intraductal papillary mucinous neoplasm, mucinous cystic neoplasm, and acinar cell carcinoma, and pancreatic ductal cancer and the like are preferable. Examples of the types of melanoma include acral lentiginous melanoma, superficial spreading melanoma, nodular melanoma, and lentigo maligna melanoma. Acral lentiginous melanoma is predominant in Japanese, while superficial spreading melanoma is predominant in Caucasians. The stages of cancers to be tested include stage 0, stage I, stage II, stage III, and stage IV (stage IVa, stage IVb) in order from the earlier stage.

The subject is a target organism of the test method of the present invention, and the biological species thereof is not particularly limited. Examples of the biological species of the subject include various mammals such as humans, monkeys, mice, rats, dogs, cats, and rabbits, and humans are preferable.

The condition of the subject regarding cancer is not particularly limited. Examples of the subject include a subject in which whether a cancer has been developed is unknown, a subject who has no history of cancer, a subject who has a history of cancer and has been treated for the cancer, and a subject who has been determined to have a cancer (or not have a cancer) by another determination method.

The biological sample is not particularly limited as long as the biological sample can contain an antigen that binds to the antibody or the functional fragment thereof of the present invention. Examples of the biological sample include body fluids such as whole blood, serum, plasma, saliva, spinal fluid, synovial fluid, urine, tissue fluid, sweat, and tears, and samples derived from these body fluids. The samples derived from the body fluids are not particularly limited as long as the samples are prepared from the body fluids, and examples thereof include a sample obtained by, for example, concentrating or purifying an antigen to which the antibody or the functional fragment thereof of the present invention binds, from a body fluid. Preferable examples of the body fluids include whole blood, serum, and plasma. As the biological sample, one type may be used alone, or two or more types may be used in combination.

The biological sample can be collected from the subject by a method known to those skilled in the art. For example, whole blood can be collected by blood collection using a syringe or the like. The blood collection is preferably performed by medical staff such as a doctor and a nurse. Serum is a portion of blood obtained by removing blood cells and specific blood coagulation factors from the blood, and can be obtained, for example, as a supernatant after coagulation of blood. Plasma is a portion of blood obtained by removing blood cells from the blood, and can be obtained, for example, as a supernatant when blood is subjected to centrifugation under conditions that blood is not coagulated.

The antigen that binds to the antibody or the functional fragment thereof of the present invention is not particularly limited as long as the antigen is 3'-sialyl lactose that can bind to the antibody or the functional fragment thereof of the present invention, or a molecule containing 3'-sialyl lactose. The test method of the present invention comprises a step of measuring the amount or concentration of the antigen that binds to the antibody or the functional fragment thereof of the present invention, and the method is not particularly limited. Examples of the method include immunoassays. Immunoassays can be widely adopted regardless of a direct method, an indirect method, a uniform method, a non-uniform method, a competitive method, a non-competitive method, and the like. More specific examples of immunoassays include ELISA (for example, direct method, indirect method, sandwich method, competitive method, etc.), radioimmunoassay (RIA), immunoradiometric assay (IRMA), enzyme immunoassay (EIA), sandwich EIA, immunochromatography, western blot, immunoprecipitation, slot or dot blot assay, immunohistochemical staining, fluorescent immunoassay, immunoassay using avidin-biotin or streptavidin-biotin system, and immunoassay using a surface plasmon resonance (SPR) method. As the detection method, one method may be adopted alone, or two or more methods may be adopted in combination.

In the step of measuring the amount or concentration of the antigen that binds to the antibody or the functional fragment thereof of the present invention, the type of label for a labeled object to be used for detecting the antigen (for example, a labeled antibody) is not particularly limited. Examples of the label include fluorescent substances, luminescent substances, pigments, enzymes, colloidal gold, and radioisotopes. Among them, enzyme labels such as peroxidase and alkaline phosphatase are preferable from the viewpoints of safety, economy, detection sensitivity, etc.

The method for measuring and calculating the amount or concentration of the antigen that binds to the antibody or the functional fragment thereof of the present invention will be described in detail.

An example of one mode of the method includes a step of bringing the antibody or the functional fragment thereof of the present invention into contact with the biological sample collected from the subject, and a step of measuring the amount of the antigen bound to the antibody or the functional fragment thereof of the present invention.

The mode of contact with the biological sample collected from the subject is not particularly limited, and an appropriate mode can be selected according to the type of the method for measuring the amount or concentration of the antibody that binds to the antibody or the functional fragment thereof of the present invention (for example, various immunoassays, etc.).

Examples of the contact mode include a mode in which the antibody or the functional fragment thereof of the present invention and the biological sample are brought into contact with each other in a state where only one of the antibody or the functional fragment thereof of the present invention and the biological sample is fixed to a solid phase, and a mode in which the antibody or the functional fragment thereof of the present invention and the biological sample are brought into contact with each other in a state where neither the antibody or the functional fragment thereof of the present invention nor the biological sample is fixed to a solid phase. Among them, from the viewpoint of efficiency, etc., a mode in which the antibody or the functional fragment thereof of the present invention and the biological sample are brought into contact with each other in a state where only the antibody or the functional fragment thereof of the present invention is fixed to a solid phase, is preferable.

When only one of the antibody or the functional fragment thereof of the present invention and the biological sample is fixed to a solid phase, after the fixation, the solid phase is preferably washed with a solution containing tris hydroxymethylaminomethane (Tris) and/or an ether-type nonionic surfactant.

The solid phase is not particularly limited as long as the antibody or the functional fragment thereof of the present invention and the biological sample can be fixed thereto. Examples of the solid phase include plates, slides, and membranes containing polystyrene, glass, nitrocellulose, or the like as a main component. The solid phase may be coated with a component for more easily fixing the antibody or the functional fragment thereof of the present invention and the biological sample, for example, a readily reactive compound (for example, a compound having a readily reactive group, colloidal gold, etc.). Examples of the compound having a readily reactive group include compounds having a group capable of forming a covalent bond with a sugar chain or a sugar chain derivative, for example, a (1H-imidazol-1-yl) carbonyl group, a succinimidyloxycarbonyl group, an epoxy group, an aldehyde group, an amino group, a thiol group, a carboxyl group, an azide group, a cyano group, an active ester group (1H-benzotriazole-1-yloxycarbonyl group, pentafluorophenyloxycarbonyl group, paranitrophenyloxycarbonyl group, etc.), a carbonyl halide group (carbonyl chloride group, carbonyl fluoride group, carbonyl bromide group, carbonyl iodide group), and the like.

Examples of the compound having a readily reactive group include epoxysilane and polylysine.

When a solid phase coated with a readily reactive compound is used, the readily reactive compound is preferably blocked using a buffer solution containing bovine serum albumin (BSA) or the like, and the blocking time is preferably 60 minutes or longer. In addition, the blocking solution preferably contains tris hydroxymethylaminomethane (Tris) and/or an ether-type nonionic surfactant.

The mode for measuring the amount of the antigen bound to the antibody or the functional fragment thereof of the present invention is not particularly limited, and an appropriate mode can be selected according to the type of the above-described method for measuring the amount or concentration of the antibody that binds to the antibody or the functional fragment thereof of the present invention (for example, various immunoassays, etc.). The measurement can be performed, for example, by quantifying a signal derived from the label of the labeled object used. As a more specific mode, the measurement can be performed, for example, by bringing the labeled antibody or functional fragment thereof of the present invention or the labeled antibody against the antigen into contact with the antigen bound to the antibody or the functional fragment thereof of the present invention, and quantifying the signal derived from the label of the bound labeled antibody.

Based on the obtained signal amount, the amount of the antigen bound to the antibody or the functional fragment thereof of the present invention can be calculated. For example, in the case of a non-competitive method, the obtained signal amount can be used as it is as the amount of the antigen bound to the antibody or the functional fragment thereof of the present invention. In addition, as another example, in the case of a competitive method, since the obtained signal amount and the amount of the antigen bound to the antibody or the functional fragment thereof of the present invention are inversely proportional to each other, the amount of the antigen bound to the antibody or the functional fragment thereof of the present invention can be calculated from a signal amount obtained based on this relationship.

According to the test method of the present invention, it is possible to provide a value of the antigen that binds to the antibody or the functional fragment thereof of the present invention, which is an index for detecting development of a cancer such as pancreatic cancer, whereby it is possible to assist in determining the possibility of having developed a cancer such as pancreatic cancer.

As one mode, the test method of the present invention preferably further comprises a step of determining that the possibility of having developed a cancer such as pancreatic cancer in the subject is high, when the measured value of the amount or concentration of the antigen that binds to the antibody or the functional fragment thereof of the present invention is equal to or higher than a preset cutoff value. Here, the "possibility of having developed a cancer such as pancreatic cancer" means the "possibility of having developed a cancer such as pancreatic cancer at the time when the biological sample is collected".

According to the test method of the present invention, it is possible to determine the possibility of having developed pancreatic cancer. In addition, with the test method of the present invention, the possibility of having developed a cancer such as pancreatic cancer can be determined with higher sensitivity, and thus a subject truly having developed a cancer such as pancreatic cancer can be more reliably determined to "have developed a cancer such as pancreatic cancer" (that is, the possibility of erroneously determining "not having developed pancreatic cancer" can be further reduced) by the test method of the present invention.

The cutoff value can be set as appropriate by those skilled in the art, from the viewpoint of sensitivity, specificity, positive predictive value, negative predictive value, etc., and can be, for example, the average value, the percentile value, or the maximum value of the amount or concentration values of the antigen that binds to the antibody or the functional fragment thereof of the present invention, in biological samples collected from subjects who have not developed a cancer such as pancreatic cancer. More specifically, for example, the cutoff value can be set by measuring the amount or concentration of the antigen that binds to the antibody or the functional fragment thereof of the present invention, in a biological sample collected from each of subjects who have not developed a cancer such as pancreatic cancer and subjects who have developed a cancer such as pancreatic cancer, and performing statistical analysis based on analysis of a receiver operating characteristic (ROC) curve and the like (more specifically, a method using a Youden index is exemplified) using the measured values.

Moreover, the cutoff value can be the amount or concentration value of the antigen that binds to the antibody or the functional fragment thereof of the present invention, in a biological sample collected from the same subject before a certain period of time. The "certain period of time" is not particularly limited as long as the certain period of time is a period in which the amount or concentration of the antigen that binds to the antibody or the functional fragment thereof of the present invention can change within the same subject. Examples of the certain period of time include periods of about 1 month to 10 years, 2 months to 5 years, 3 months to 2 years, and 4 months to 1 year.

A modification of the test method of the present invention is a method comprising a step of determining that the subject is likely to develop a cancer such as pancreatic cancer in the future, when the amount or concentration value of the antigen that binds to the antibody or the functional fragment thereof of the present invention is higher than the amount or concentration value of the antigen that binds to the antibody or the functional fragment thereof of the present invention, in a biological sample collected from the same subject before a certain period of time. The risk of developing pancreatic cancer in the future is determined by the test method including this step.

The "certain period of time" is not particularly limited as long as the certain period of time is a period in which the amount or concentration of the antigen that binds to the antibody or the functional fragment thereof of the present invention can change within the same subject. Examples of the certain period of time include periods of about 1 month to 10 years, 2 months to 5 years, 3 months to 2 years, and 4 months to 1 year.

The degree of "higher" is not particularly limited, and examples thereof include the amount or concentration value of the antigen that binds to the antibody or the functional fragment thereof of the present invention being 2 times or more, 4 times or more, 8 times or more, and 20 times or more the amount or concentration value of the antigen that binds to the antibody or the functional fragment thereof of the present invention, in the biological sample collected from the same subject before the certain period of time.

When it is determined by the test method of the present invention that the possibility of having developed a cancer such as pancreatic cancer in the subject is high, development of a cancer such as pancreatic cancer can be diagnosed with higher accuracy by further combining the test method of the present invention with another diagnostic method. The other diagnostic method is not particularly limited, and various known diagnostic methods can be adopted. Examples of the diagnostic method include a biopsy method, a PET test method, a CT test method, an ultrasonic test method, and a tumor marker test method. Among them, from the viewpoint of being able to diagnose pancreatic cancer with higher accuracy, a biopsy method, a PET test method, a CT test method, an ultrasonic test method, and the like are preferable. As the diagnostic method, one method may be adopted alone, or two or more methods may be adopted in combination.

The test drug of the present invention may be in the form of a composition comprising the antibody or the functional fragment thereof of the present invention. The composition may contain other components, if necessary. Examples of the other components include a base, a carrier, a solvent, a dispersant, an emulsifier, a buffer, a stabilizer, an excipient, a binder, a disintegrant, a lubricant, a thickener, a moisturizer, a colorant, a flavor, and a chelating agent.

The test drug of the present invention may be in the form of a kit comprising the antibody or the functional fragment thereof of the present invention. The kit may comprise instruments, reagents, and the like that can be used to carry out the test method of the present invention.

Examples of the instruments include a test tube, a microtiter plate, agarose particles, latex particles, a column for purification, an epoxy-coated slide glass, and a colloidal gold-coated slide glass.

Examples of the reagents include an antibody against the antigen of the antibody of the present invention or a labeled antibody thereof, and standard samples (positive control, negative control).

As the antibody against the antigen of the antibody of the present invention, an antibody against 3'-sialyl lactose, an antibody against a molecule (for example, protein) to which the antibody of the present invention binds, etc., can be used.

The type of the label for producing the labeled antibody is not particularly limited. Examples of the label include fluorescent substances, luminescent substances, pigments, enzymes, colloidal gold, and radioisotopes. Among them, enzyme labels such as peroxidase and alkaline phosphatase are preferable from the viewpoints of safety, economy, detection sensitivity, etc.

As a standard sample, the antigen of the antibody of the present invention is used. The antigen of the antibody of the present invention can be separated and purified, for example, by an immunoprecipitation method from the biological sample using the antibody of the present invention. In addition, the antigen of the antibody of the present invention can be obtained by producing a polymer containing 3'-sialyl lactose (for example, 3'-sialyl lactose PAA, manufactured by GlycoTech Corporation), a liposome or protein having 3'-sialyl lactose exposed on the surface thereof, or the like.

The present invention also provides a pharmaceutical composition for diagnosing a disease, comprising the antibody or the functional fragment thereof of the present invention labeled with a diagnostic agent. When it is determined by the test method of the present invention that the possibility of having developed a cancer such as pancreatic cancer in the subject is high, development of a cancer such as pancreatic cancer can be diagnosed with higher accuracy by, for example, intravascularly, intramuscularly, subcutaneously, or intraperitoneally administering the pharmaceutical composition comprising the antibody or the functional fragment thereof of the present invention labeled with the diagnostic agent, and examining the whole body.

The pharmaceutical composition for diagnosing a disease of the present invention can further comprise a pharmaceutically acceptable carrier. Examples of pharmaceutically acceptable carriers that can be used include standard pharmaceutical carriers known in the art such as phosphate-buffered saline solutions, water, emulsions including oil/water emulsions and the like, and various types of wetting agents. In addition, other components, such as a pharmaceutical-grade stabilizer, buffer, preservative, and excipient, can also be used in the pharmaceutical composition for diagnosing a disease of the present invention, and preparation of the pharmaceutical composition in consideration of pH, isotonicity, stability, etc., can be carried out by a known method.

Examples of the diagnostic agent for labelling the antibody or the functional fragment thereof of the present invention include radioactive substances, fluorescent materials, luminescent materials, bioluminescent materials, and photoacoustic imaging materials. Examples of radioactive substances include various positron emitting metals such as zirconium ($^{89}$Zr), iodine ($^{131}$I, $^{125}$I, $^{124}$I, $^{123}$I, and $^{121}$I) indium ($^{115}$In, $^{113}$In, $^{112}$In, and $^{111}$In), technetium ($^{99}$Tc), thallium ($^{201}$Ti) and gallium ($^{68}$Ga, $^{67}$Ga). Examples of luminescent materials include umbelliferone, fluorescein, and fluorescein isothiocyanate. Examples of luminescent materials include luminol. Examples of bioluminescent materials include luciferase, luciferin, and aequorin. Examples of photoacoustic imaging materials include gold nanoparticles, single-layer carbon nanotubes, indocyanine green, and methylene blue.

Examples of the method for labeling the antibody or the functional fragment thereof of the present invention include a method of indirectly binding a compound using a linker such as polyethylene glycol, and a method of directly binding a compound by forming a disulfide bond at a cysteine residue of the antibody or the functional fragment thereof. It is also possible to directly bind a compound to the antibody or the functional fragment thereof using a heterologous bifunctional crosslinking agent such as N-succinyl-3-(2-pyridyldithio)propionate. Furthermore, a compound can also be bound by oxidizing the sugar chain in the Fc region of the antibody.

The dose of the antibody or the functional fragment thereof labeled with the diagnostic agent, which is contained in the pharmaceutical composition for diagnosing a disease of the present invention, is not particularly limited as long as the dose is a pharmacologically effective amount. The dose can be determined as appropriate according to race, gender, age, type of cancer, etc., and is usually 0.01 to 1,000 mg/kg and preferably 0.1 to 100 mg/kg. The time required to preferentially concentrate the antibody or the functional fragment thereof of the present invention labeled with the diagnostic agent, on the binding site in the subject, and to remove the antibody or the functional fragment thereof not bound to the binding site, to the background level, can be determined as appropriate according to the type of the diagnostic agent to be used, the administration method, etc., and is, for example, about 6 to 48 hours after administration. In addition, when the disease is monitored, the disease is repeatedly monitored, for example, at a time interval of 5 to 20 days after administration, for 1 to 12 months from the first diagnosis.

The presence of the antibody or the functional fragment labeled with the diagnostic agent, which is contained in the pharmaceutical composition for diagnosing a disease of the present invention, can be detected by examining the whole body of the subject using a known method. The detection method depends on the type of the diagnostic agent to be used, and examples of methods that can be used in the present invention include computed tomography, positron emission tomography, magnetic resonance imaging, ultrasonography, and photoacoustic imaging.

Examples of diseases that can be diagnosed using the pharmaceutical composition of the present invention include cancers such as the pancreatic cancer described above, and the pharmaceutical composition of the present invention is particularly useful for diagnosing a cancer that highly expresses 3'-sialyl lactose. That is, when it is determined by the test method of the present invention that the possibility of having developed a cancer such as pancreatic cancer in the subject is high, it is possible to diagnose a cancer such as pancreatic cancer in the subject with higher accuracy by administering the pharmaceutical composition of the present invention.

3. Cancer Treatment

When it is determined by the test method of the present invention that the possibility of having developed a cancer such as pancreatic cancer in the subject is high, or when the subject is diagnosed to have a cancer in combination with another diagnostic method, it is possible to treat the subject's cancer by performing cancer treatment on the subject. In addition, with the test method of the present invention, the possibility of having developed cancer such as pancreatic cancer can be determined with higher sensitivity, so that a subject truly having developed a cancer can be treated more reliably (that is, the possibility of excluding the subject truly having developed a cancer from subjects to be treated can be reduced) by the test method of the present invention or by a combination with another diagnostic method.

The method of the cancer treatment is not particularly limited, and various known treatment methods can be adopted. Examples of the treatment method include chemotherapy, surgical treatment, radiotherapy, and immunotherapy. These treatments can be carried out according to known methods.

The therapeutic agent used for chemotherapy is not particularly limited, and various anticancer agents can be used. Examples of anticancer agents include alkylating agents, antimetabolites, microtubule inhibitors, antibiotic anticancer agents, topoisomerase inhibitors, platinum preparations, molecular target drugs, hormone agents, and biological preparations. Examples of the alkylating agents include cyclophosphamide, ifosfamide, nitrosourea, dacarbazine, temozolomide, nimustine, busulfan, melphalan, procarbazine, and ranimustine. Examples of the antimetabolites include enocitabine, carmofur, capecitabine, tegafur, tegafur-uracil, tegafur-gimeracil-oteracil potassium, gemcitabine, cytarabine, cytarabine ocfosfate, nelarabine, fluorouracil, fludarabine, pemetrexed, pentostatin, methotrexate, cladribine, doxifluridine, hydroxycarbamide, and mercaptopurine. Examples of the microtubule inhibitors include alkaloid-based anticancer agents such as vincristine and taxane-based anticancer agents such as docetaxel and paclitaxel. Examples of the antibiotic anticancer agents include mitomycin C, doxorubicin, epirubicin, daunorubicin, bleomycin, actinomycin D, aclarubicin, idarubicin, pirarubicin, peplomycin, mitoxantrone, amrubicin, and zinostatin stimalamer. Examples of the topoisomerase inhibitors include CPT-11, irinotecan, and nogitecan having topoisomerase I inhibitory action, and etoposide and sobuzoxane having topoisomerase II inhibitory action. Examples of the platinum preparations include cisplatin, nedaplatin, oxaliplatin, and carboplatin. Examples of the hormone agents include dexamethasone, finasteride, tamoxifen, anastrozole, exemestane, ethinylestradiol, chlormadinone, goserelin, bicalutamide, flutamide, prednisolone, leuprorelin, letrozole, estramustine, toremifene, fosfestrol, mitotane, methyltestosterone, medroxyprogesterone, and mepitiostane. Examples of the biological preparations include immune checkpoint inhibitors such as anti-PD-1 antibody and anti-PD-L1 antibody, interferons α, β, and γ, interleukin 2, ubenimex, and dried BCG. Examples of the molecular target drugs include rituximab, alemtuzumab, trastuzumab, cetuximab, panitumumab, imatinib, dasatinib, nilotinib, gefitinib, erlotinib, temsirolimus, bevacizumab, VEGF trap, sunitinib, sorafenib, tocilizumab, bortezomib, gemtuzumab-ozogamicin, ibritumomab-ozogamicin, ibritumomab tiuxetan, tamibarotene, and tretinoin. In addition to the molecular target drugs specified here, the following molecular target drugs may be included: inhibitors targeting angiogenesis such as human epidermal growth factor receptor 2 inhibitor, epidermal growth factor receptor inhibitor, Bcr-Abl tyrosine kinase inhibitor, epidermal growth factor tyrosine kinase inhibitor, mTOR inhibitor, and endothelial growth factor receptor 2 inhibitor (α-VEGFR-2 antibody); tyrosine kinase inhibitors such as MAP kinase inhibitor; inhibitors targeting cytokine, proteasome inhibitors, and antibody-anticancer agent formulations. These inhibitors also include antibodies.

Typical pancreatic cancer therapeutic agents include gemcitabine, TS-1, erlotinib, a concomitant drug of gemcitabine and erlotinib, a concomitant drug of gemcitabine and albumin-bound paclitaxel, and a concomitant drug of four drugs (oxaliplatin, levofolinate, irinotecan, and fluorouracil).

The present invention also provides a pharmaceutical composition for treating a disease, comprising the antibody or the functional fragment thereof of the present invention. As shown in Examples described later, the antibody or the functional fragment thereof of the present invention itself has cancer cytotoxic activity, so that the antibody or the functional fragment thereof of the present invention alone can be used to treat a cancer such as pancreatic cancer. The present invention further provides a pharmaceutical composition for treating a disease, comprising the antibody or the functional fragment thereof of the present invention labeled with a therapeutic agent such as the above various anticancer agents and pancreatic cancer therapeutic agents, toxin compounds including lysine and the like, and radioactive substances including radioactive metal ions (for example, compounds having radioactive activity such as alpha emitter) and the like. Examples of the method for labeling include a method of indirectly binding a compound using a linker such as polyethylene glycol, and a method of directly binding a compound by forming a disulfide bond at a cysteine residue of the antibody or the functional fragment thereof. It is also possible to directly bind a compound to the antibody or the functional fragment thereof using a heterologous bifunctional crosslinking agent such as N-succinyl-3-(2-pyridyl-dithio)propionate. Furthermore, a compound can also be bound by oxidizing the sugar chain in the Fc region of the antibody.

The pharmaceutical composition for treating a disease of the present invention can further comprise a pharmaceutically acceptable carrier. Examples of pharmaceutically acceptable carriers that can be used include standard pharmaceutical carriers known in the art such as phosphate-buffered saline solutions, water, emulsions including oil/water emulsions and the like, and various types of wetting agents. In addition, other components, such as a pharmaceutical-grade stabilizer, buffer, preservative, and excipient, can also be used in the pharmaceutical composition for treating a disease of the present invention, and preparation of the pharmaceutical composition in consideration of pH, isotonicity, stability, etc., can be carried out by a known method.

The dose of the antibody or the functional fragment thereof contained in the pharmaceutical composition for treating a disease of the present invention and the dose of the antibody or the functional fragment thereof labeled with the therapeutic agent are not particularly limited as long as each of the doses is a pharmacologically effective amount. Each of the doses can be determined as appropriate according to race, gender, age, type of cancer, etc., and each of the antibodies or the functional fragments thereof can usually be administered at 0.01 to 1,000 mg/kg and preferably at 0.1 to 100 mg/kg once every 1 to 180 days, or twice or three times or more a day.

Examples of diseases that can be treated using the pharmaceutical composition of the present invention include cancers such as the pancreatic cancer described above, and the pharmaceutical composition of the present invention is particularly useful for treating a cancer that highly expresses 3'-sialyl lactose. That is, when it is determined by the test method of the present invention that the possibility of having developed a cancer such as pancreatic cancer in the subject is high, it is possible to treat a cancer such as pancreatic cancer in the subject by administering the pharmaceutical composition of the present invention.

EXAMPLES

Hereinafter, the present invention will be described in detail based on examples, but the present invention is not limited to these examples, etc.

Example 1. Preparation of Mouse Monoclonal Antibody Against Human ES Cells (a) Preparation of Hybridomas Human ES cells (clone name: KhES-1) were cultured on mitomycin-treated mouse primary fibroblasts (manufactured by Oriental Yeast Co., Ltd., catalog number: KBL9284400) in a DMEM/F12 medium (manufactured by Sigma-Aldrich, catalog number: D9785) containing additives (20% KSR (KnockOut Serum Replacement, manufactured by Invitrogen, catalog number: 10828028), 2 mM glutamine, 0.1 mM non-essential amino acids) to maintain undifferentiated potential. A PBS (phosphate buffered saline) containing an enzyme solution (0.25% trypsin, 1 mg/ml collagenase IV, 20% KSR, 1 mM $CaCl_2$) was added to the undifferentiated human ES cells, and the cells were peeled off by pipetting, and centrifuged (1000 rpm, 3 minutes). The PBS was added to the undifferentiated human ES cells as the precipitate to suspend the cells, then twice the amount of ADJUBANT COMPLETE FREUND (manufactured by DIFCO, catalog number: 263810) was added, and the mixture was sonicated and emulsified to prepare an immune source.

50 µl of the immune source was injected into the ridge of an 8-week-old female C57BL/6JJmsSl mouse, and, 14 days later, booster immunization was performed with a suspension obtained by suspending the undifferentiated human ES cells in PBS, as an immune source. Three days after the booster immunization, lymphocytes were collected from the abdominal lymph nodes, the number of lymphocyte cells was measured, and then $1 \times 10^8$ lymphocytes and $2 \times 10^7$ mouse myeloma SP2 cells were mixed and centrifuged (1300 rpm, 10 minutes). 1 ml of PEG1500 (manufactured by Roche, catalog number: 783641) was added to the precipitate, and the mixture was kept warm at 37° C. for 2 minutes to perform cell fusion. Then, 4.5 ml of a DMEM medium (manufactured by FUJIFILM Wako Pure Chemical Corporation, catalog number: 044-29765) was added, and the mixture was centrifuged. Next, 50 ml of a HAT medium (Hybridoma-SFM (manufactured by GIBCO, catalog number: 12300-067) containing hypoxanthine 13.61 mg/l, aminopterin 0.176 mg/l, thymidine 3.88 mg/l, bovine fetal serum 10%) was added to the precipitate and mixed. Then, 100 µl of the hybridoma suspension was seeded per well on four 96-well plates and cultured for 5 days.

(b) Screening of Hybridomas

The undifferentiated human ES cells were cultured on mouse primary fibroblasts in a 96-well plate, then 37% formaldehyde (manufactured by FUJIFILM Wako Pure Chemical Corporation, catalog number: 06400406) diluted 10-fold with PBS was added thereto, and fixation was performed at room temperature for 15 minutes. After washing once with PBS, 50 µl of 0.5% Triton-X 100 was added per well, and the plate was allowed to stand at room temperature for 5 minutes. After washing 3 times with PBS, an NGS blocking solution (PBS solution containing 1% BSA, 2% goat serum, and 3.75% glycine) was added, and the plate was allowed to stand at room temperature for 30 minutes. Next, the NGS blocking solution was removed, 40 µl of the hybridoma supernatant in (a) of Example 1 was added, and the plate was allowed to stand at room temperature for 1 hour. After washing 3 times with PBS, goat anti-mouse IgG (H+L)-Alexa Fluor 488 (manufactured by Abcam, catalog number: ab150113) diluted 500-fold with the NGS blocking solution was added, and the plate was allowed to stand at room temperature for 30 minutes. Next, after washing 3 times with PBS, 50 µl of PBS was added per well, and a fluorescence image was observed with a fluorescence microscope to screen hybridoma supernatants in which only undifferentiated human ES cells were stained, not mouse primary fibroblasts.

The hybridomas were collected from the wells containing the screened supernatants, 10 ml of the HAT medium was added per 100 hybridomas, and 100 µl of the mixture was added per well (theoretically, 1 hybridoma per well) to a 96-well plate, and cultured. The hybridoma supernatants were screened by immunostaining in the same manner as above. As a result, clone 3B1E2 that produces an antibody that reacts with the undifferentiated human ES cells was obtained.

(c) Purification of 3B1E2 Antibody

Clone 3B1E2 was expanded and propagated in a HAT medium for propagation. After propagation to a 10 cm petri dish, clone 3B1E2 was cultured with the fetal bovine serum in the HAT medium being gradually lowered from 10% to 5%, 2%, 1%, and 0%, re-seeded into a 15 cm petri dish, and cultured in a HAT medium containing no fetal bovine serum for 12 days.

Ammonium sulfate and 1/10 volume of 1 M Tris-HCl (pH 8.0) were added to the obtained culture supernatant to have a concentration of 314 g/l, and the mixture was stirred at room temperature for 1 hour. The mixture was centrifuged (18,000 rpm, 4° C., 30 minutes), and 2 ml of a 15.7 mM phosphate buffer solution (pH 6.3) containing 20 mM NaCl was added to the obtained precipitate to completely dissolve the precipitate, and the solution was applied to a PD-10 column (manufactured by GE Healthcare, catalog number: 17-0851-01) and then eluted with 2.5 ml of the same buffer solution. The obtained eluate was then applied to a HiTrap SP HP strong ion exchange column (manufactured by GE Healthcare, catalog number: 17-1151-01), and eluted and fractionated with a 15.7 mM phosphate buffer solution (pH 6.3) containing 1 M NaCl. Each fraction was subjected to SDS-PAGE to obtain an antibody fraction, and the protein concentration was determined using BCA Protein Assay Kit (manufactured by Thermo Fisher Scientific, catalog number: 23225). Moreover, when the class of the antibody was determined using Mouse Monoclonal Antibody Isotyping Test Kit (manufactured by BioRad, catalog number: MMT1), it was IgM, κ.

(d) Determination of 3B1E2 Antibody Gene

Total RNA was purified from clone 3B1E2 using ISO-GEN II (manufactured by Nippon Gene Co., Ltd., catalog number: 311-07361), and a primer for a heavy chain or light chain constant region of mouse IgM (Mu IgM $V_H$ 3'-1 Primer or Mu Igκ $V_L$ 3'-1 Primer: manufactured by Merck, catalog number: 69831-3CN) and a reverse transcriptase (manufactured by Thermo Fisher Scientific, catalog number: 18080044) were added to the total RNA, and reacted at 55° C. for 30 minutes to prepare cDNA. PCR was performed using the obtained cDNA and Mu Ig $V_H$ 5'-F Primer and Mu IgM $V_H$ 3'-1 Primer of Mouse Ig-Primer Set (manufactured by Merck, catalog number: 69831-3CN), or Mu Igκ VL 5'-G Primer and Mu Igκ VL 3'-1 Primer, to obtain mouse antibody gene fragments of about 500 bp of a heavy chain and a light chain, respectively. The obtained gene fragments were inserted into pGEM-T Easy vector (manufactured by Promega, catalog number: A1360) and cloned.

The CDR base sequences of the heavy chain and the light chain of a 3B1E2 antibody were determined by a DNA sequencer, and the amino acid sequences of the CDR1 to 3 of the heavy chain and the light chain shown in Table 1 were identified. In addition, the amino acid sequences and the base sequences of the entire heavy chain variable region and the entire light chain variable region are shown below.

TABLE 1

| SEQ ID NO: | Sequence name | Amino acid sequence |
|---|---|---|
| 1 | Heavy chain variable region CDR1 | GIDFSIYW |
| 2 | Heavy chain variable region CDR2 | INSDSSTI |
| 3 | Heavy chain variable region CDR3 | ARKNGGLDYAMDY |
| 4 | Light chain variable region CDR1 | KSISKY |
| — | Light chain variable region CDR2 | SGS |
| 5 | Light chain variable region CDR3 | QQHNEYPWT |

```
Heavy chain variable region
(amino acid sequence)
                                (SEQ ID NO: 11)
MDFGLIFFIVALLKGVQCEVKLLQSGGGLVQPGGS

LKLSCAASGIDFSIYWMSWVRRAPGKGLEWIGEIN

SDSSTINYAPSLKDKFTISRDNAKNTLYLQMSKVR

SEDTALYYCARKNGGLDYAMDYWGQGTSVTVSS

Light chain variable region
(amino acid sequence)
                                (SEQ ID NO: 12)
MVLISLLFWISGAQCDVQITQSPSYLAASPGETIT

INCRSSKSISKYLAWYQEKPGKTNKLLIYSGSTLQ

SGIPSRFSGSGSGTDFTLTISSLEPEDFAMYYCQQ

HNEYPWTFGGGTKLEIK

Heavy chain variable region
(base sequence)
                                (SEQ ID NO: 13)
ATGGATTTTGGGCTGATTTTTTTTATTGTTGCTCT

TTTAAAAGGGGTCCAGTGTGAGGTGAAGCTTCTCC

AGTCTGGAGGTGGCCTGGTGCAGCCTGGAGGATCC

CTGAAACTCTCCTGTGCAGCCTCAGGAATCGATTT

TAGTATATACTGGATGAGTTGGGTTCGGCGGGCTC

CAGGGAAAGGACTAGAATGGATTGGAGAAATTAAT

TCAGATAGCAGTACAATAAACTATGCACCATCTCT

AAAGGATAAATTCACCATCTCCAGAGACAACGCCA

AAAATACGCTGTACCTGCAAATGAGCAAAGTGAGA

TCTGAGGACACAGCCCTTTATTACTGTGCAAGAAA

GAATGGGGGATTGGACTATGCTATGGACTACTGGG

GTCAAGGAACCTCAGTCACCGTCTCCTCA

Light chain variable region
(base sequence)
                                (SEQ ID NO: 14)
ATGGTTCTCATATCCTTGCTGTTCTGGATATCAGG

TGCCCAGTGTGATGTCCAGATAACCCAGTCTCCAT

CTTATCTTGCTGCATCTCCTGGAGAAACCATTACT
```

-continued

```
ATTAATTGCAGGTCAAGTAAGAGCATTAGCAAATA

TTTAGCCTGGTATCAAGAGAAACCTGGGAAAACTA

ATAAGCTTCTTATCTACTCTGGATCCACTTTACAA

TCTGGAATTCCATCAAGGTTCAGTGGCAGTGGATC

TGGTACAGATTTCACTCTCACCATCAGTAGCCTGG

AGCCTGAAGATTTTGCAATGTATTACTGTCAACAG

CATAATGAATACCCGTGGACGTTCGGTGGAGGCAC

CAAGCTGGAAATCAAG
```

(e) Preparation of 3B1E2 Antibody (Mouse IgG2a, κ)

The gene fragment of the heavy chain or light chain variable region obtained in (d) of Example 1 was inserted into a mouse antibody (IgG2a) expression vector pUC19-CAG-HC (mIgG2a) or pUC19-CAG-HC (mKappa), respectively. 0.25 μg of each of the two prepared plasmids was introduced into HEK293 cells that were $0.4 \times 10^6$ cells, using PEI (manufactured by Merck, catalog number: 408727-100ML), and cultured for 3 days. The obtained culture supernatant was collected, and ammonium sulfate and 1 M Tris-HCl (pH 8.0) were added in the same manner as in (c) of Example 1 to prepare a 3B1E2 antibody (mouse IgG2a, κ).

Example 2. Binding of 3B1E2 Antibody and 3'-sialyl Lactose

100 μl of a PBS solution of 3'-sialyl lactose-PAA (polyacrylamide) (manufactured by GlycoTech Corporation, catalog number 08-038) in 10 μg/ml was added to each well of a MaxiSorp 96-well plate (manufactured by Thermo Fisher Scientific, catalog number: 439454), and the plate was allowed to stand at room temperature for 16 hours. Next, each well was washed 3 times with 300 μl of a PBS (washing liquid) containing 1% Triton-X 100, then 200 μl of a PBS containing 5% BSA and 1% Triton-X 100 was added to each well, and the plate was allowed to stand at room temperature for 1 hour. Each well was washed with 300 μl of the washing liquid, then 100 μl of a 3B1E2 antibody (mouse IgG2a or mouse IgM)) or a control antibody (mouse IgG2a: manufactured by BioLegend, catalog number: 401502, or mouse IgM: manufactured by BioLegend, catalog number: 401602) was added to each well, and the plate was allowed to stand at room temperature for 2 hours.

Next, each well was washed 5 times with 300 μl of the washing liquid, then 100 μl of peroxidase-labeled goat anti-mouse IgG antibody (manufactured by Jackson Immuno Research, catalog number: 115-035-071) or peroxidase-labeled goat anti-mouse IgM antibody (manufactured by Jackson ImmunoResearch, catalog number: 115-035-075) diluted 1,000 times was added to each well, and the plate was allowed to stand at room temperature for 1 hour. Then, after washing 3 times with 300 μL of the washing liquid, 100 μl of a peroxidase substrate solution (manufactured by SeraCare Life Sciences, catalog number: 5120-0053) was added to each well, and the plate was allowed to stand at room temperature for 30 minutes. After the reaction, 50 μl of 2% sulfuric acid was added to stop the reaction, and then the absorbance at 450 nm in each well was measured with a microplate reader.

Figure 2:
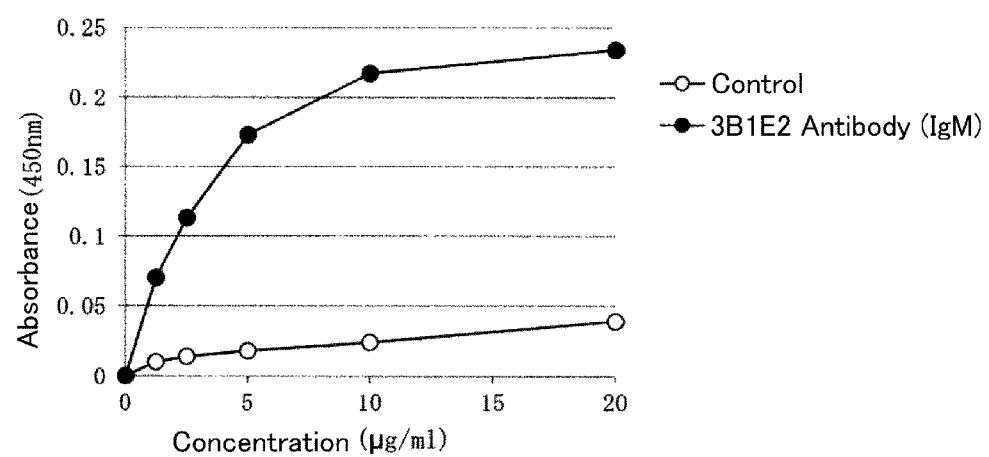
FIG. 2 shows the results of binding of a 3B1E2 antibody (mouse IgM) and 3'-sialyl lactose performed in Example 2, in which the vertical axis represents absorbance at 450 nm and the horizontal axis represents the concentration of the antibody.

As a result, as shown in FIG. 1, it was shown that the 3B1E2 antibody (mouse IgG2a) was more strongly bound to 3'-sialyl lactose than the control antibody. Moreover, as shown in FIG. 2, it was shown that the 3B1E2 antibody (mouse IgM) was more strongly bound to 3'-sialyl lactose than the control antibody.

Example 3. Pathological Examination of Cancer Tissue by 3B1E2 Antibody

A tissue array slide (manufactured by US Biomax, catalog number: MC5003c) on which sections of cancer tissue (about 15 specimens for each type) for multiple types of tissues had been placed was deparaffinized (xylene for 7 minutes 3 times, methanol for 2 minutes 3 times, washing with water), and then methanol containing 3% hydrogen peroxide was added to inactivate the endogenous peroxidase. After washing with water, the tissue array slide was kept warm in a 10 mM citrate buffer solution (pH 6.0) at 98° C. for 5 minutes to activate the antigen. After washing, each specimen was encircled with a Pap pen, and then a Block Ace (manufactured by DS Pharma Biomedical Co., Ltd., catalog number: UKB40) solution was added thereto, and blocking treatment was performed at room temperature for 15 minutes.

Next, 300 μl of 50 μg/ml 3B1E2 antibody (mouse IgG2a) was added, and the slide was allowed to stand at room temperature for 2 hours. After washing 3 times with PBS, Histofine Simple Stain MAX-PO for human tissues (manufactured by Nichirei Corporation, catalog number: 424131) was added, and the slide was allowed to stand at room temperature for 30 minutes. After washing 3 times with PBS, a DAB coloring solution (manufactured by Dako, catalog number: K3468) was added and reacted for 1 minute. Then, washing was performed with water, a hematoxylin solution (manufactured by Sakura Finetek Japan Co., Ltd., catalog number: 8656) was added, and the nucleus was stained for about 30 seconds. After washing with water, the slide was dehydrated (75% ethanol for 3 minutes, 95% ethanol for 3 minutes, 100% ethanol for 3 minutes twice), cleared (xylene for 3 minutes twice), then sealed, and observed with a microscope.

As a result of measuring the ratio of positive specimens stained with the 3B1E2 antibody (mouse IgG2a) to all the specimens, as shown in Table 2, 50% or more of the specimens were positive for pancreatic cancer and melanoma, and 10% or more of the specimens were positive for thyroid cancer, gastric cancer, testicular cancer, and ovarian cancer. From this, it was shown that the antigen of the 3B1E2 antibody is detected in cancer tissues of pancreatic cancer, melanoma, thyroid cancer, gastric cancer, testicular cancer, and ovarian cancer.

TABLE 2

| Cancer | Ratio of positive specimens |
| --- | --- |
| Pancreatic | ++ |
| Melanoma | ++ |
| Thyroid | + |
| Gastric | + |
| Testicular | + |
| Ovarian | + |

++: 50% or more,
+: 10% or more

Example 4. Blood Test of Pancreatic Cancer Patients by 3B1E2 Antibody (a) Peroxidase Labeling of 3B1E2 Antibody (Mouse IgM)

10 μg of the 3B1E2 antibody (mouse IgM) was labeled with peroxidase according to the protocol using Ab-10 Rapid Peroxidase Labeling Kit (manufactured by DOJINDO LABORATORIES, catalog number: LK33).

(b) Preparation of Serum Samples

As biological samples, the sera of 13 healthy subjects and 55 pancreatic cancer patients (stage I: 15 patients, stage II: 15 patients, stage III: 11 patients, stage IV: 14 patients) were obtained from a hospital in the US through FUJIFILM Wako Pure Chemical Corporation. Each serum was diluted 6-fold with a sample dilution solution (PBS containing 1% BSA and 0.05% Triton-X 100) to prepare a serum sample.

(c) Measurement of Antigen Value of 3B1E2 Antibody in Sera of Healthy Subjects and Pancreatic Cancer Patients 100 μl of the 3B1E2 antibody (mouse IgG2a) in 10 μg/ml was added to each well of a MaxiSorp 96-well plate, and the plate was allowed to stand at 4° C. for 16 hours. Next, each well was washed 3 times with 200 μl of a washing liquid (50 mM Tris-HCl (pH 8.0) containing 0.05% Triton-X 100, 140 mM NaCl), 200 μl of a washing liquid containing 5% BSA was added to each well, and the plate was allowed to stand at room temperature for 1 hour. Each well was washed 3 times, 100 μl of a serum sample was added to each well, and the plate was allowed to stand at room temperature for 1 hour. Then, each well was washed 5 times, 100 μl of peroxidase-labeled 3B1E2 antibody (mouse IgM) diluted 10,000 times with a sample dilution solution was added to each well, and the plate was allowed to stand at room temperature for 1 hour. Each well was washed 5 times, then 100 μl of a peroxidase substrate solution (manufactured by SeraCare Life Sciences, code number: 5120-0053) was added to each well, and the plate was allowed to stand at room temperature for 30 minutes. After the reaction, 50 μl of 2% sulfuric acid was added to stop the reaction, and the absorbance at 450 nm in each well was measured with a microplate reader.

Figure 3:
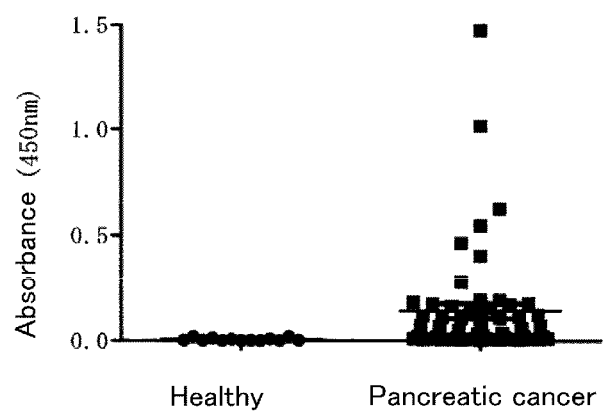
FIG. 3 shows the antigen values of 3B1E2 antibody in the sera of healthy subjects and pancreatic cancer patients in Example 4, in which the vertical axis represents the antigen value of the 3B1E2 antibody (the numerical value is the absorbance at 450 nm).

As a result, as shown in FIG. 3, it was shown that, in the pancreatic cancer patients, the antigen value of the 3B1E2 antibody in the serum was significantly higher ($p<0.0001$) than in the healthy subjects, and development of pancreatic cancer and the antigen value of the 3B1E2 antibody correlate with each other.

Example 5. Injury Effect of 3B1E2 Antibody on Cancer Cells

A 3B1E2 antibody binds to the cell membrane surface of human pancreatic cancer cell line KP-3L (JCRB biological resource bank, cell registration number: JCRB0178.1). KP-3L was dispersed in an RPMI-1640 medium (manufactured by FUJIFILM Wako Pure Chemical Corporation, code number: 186-02155) containing 1% bovine serum albumin (manufactured by Sigma-Aldrich, catalog number: A7906), and $2\times10^4$ KP-3L cells were seeded per well on a 96-well culture plate. The next day, 35 μl of the medium was removed, and 10 μl of an RPMI-1640 medium containing the 3B1E2 antibody (mouse IgG2a) or a control antibody (manufactured by BioLegend, catalog number: 401502) was added, and the plate was allowed to stand at room temperature for 30 minutes. Next, 25 μl of a rabbit complement serum (manufactured by Sigma-Aldrich, catalog number: 57764) was added and cultured at 37° C. under 5% $CO_2$ for 4 hours. Then, the plate was centrifuged at 1,000 rpm for 5 minutes, 50 μl of the supernatant was collected, and the lactose dehydrogenase activity in the supernatant was measured using a cytotoxicity detection kit (manufactured by Roche, catalog number: 4744926). An RPMI-1640 medium was added instead of the antibody for negative control, an RPMI-1640 medium and Tween (trademark) 20 were added instead of the antibody and the rabbit complement serum for positive control, and measurement was performed in the same manner. The cancer cytotoxic activity of the antibody was calculated based on the following formula.

Cancer cytotoxic activity (%)=(absorbance at 485 nm of antibody−absorbance at 485 nm of negative control)/(absorbance at 485 nm of positive control−absorbance at 485 nm of negative control)×100

Figure 4:
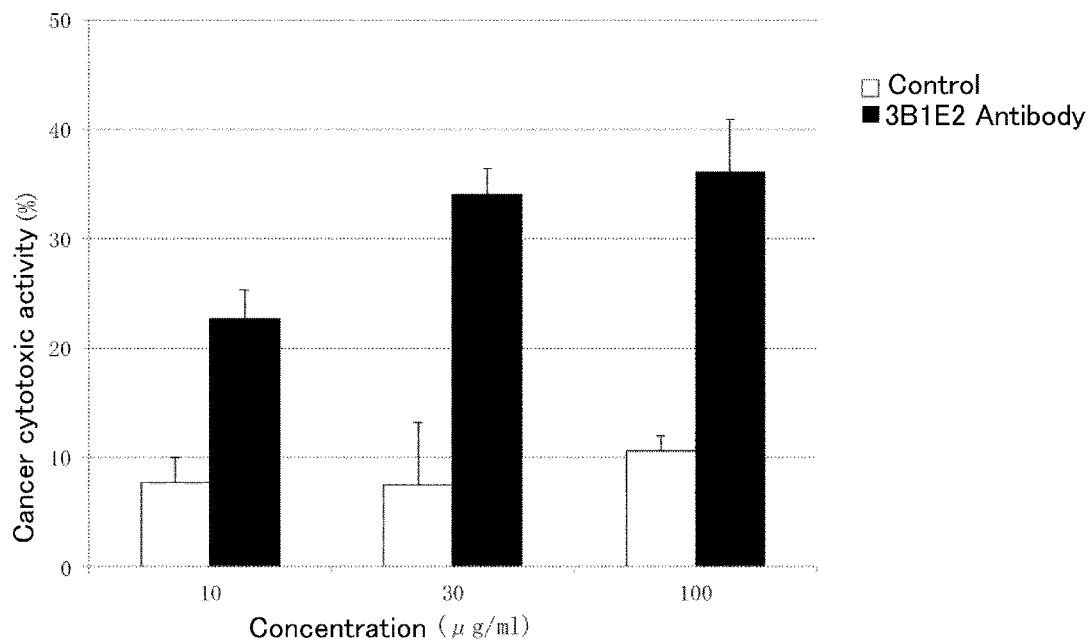
FIG. 4 shows the results of the cancer cytotoxic activity of the 3B1E2 antibody (mouse IgG2a) and a control antibody (mouse IgG2a) performed in Example 5, in which the vertical axis represents the cancer cytotoxic activity, the horizontal axis represents the concentration of the antibody, and the data are shown as mean±standard deviation. n=3

As a result, as shown in FIG. 4, it was shown that the cancer cytotoxic activity of the 3B1E2 antibody increased in a concentration-dependent manner, and the activity was significantly ($p<0.01$) higher than those of the controls at all the concentrations.

INDUSTRIAL APPLICABILITY

With the test drug using the antibody of the present invention, it is possible to determine the possibility of having developed a cancer such as pancreatic cancer. It is also possible to monitor the progression of a cancer such as pancreatic cancer and the effectiveness of anticancer agents by measuring the antigen value of the antibody of the present invention. In addition, with the pharmaceutical composition using the antibody of the present invention, it is possible to diagnose and treat a cancer such as pancreatic cancer.

[Sequence List]

P19-296WO_PCT_antibody and functional fragment thereof_20200131_111756_3.txt

The invention claimed is:

1. An antibody or a functional fragment thereof binding to 3'-sialyl lactose and comprising:
   (i) a heavy chain variable region which comprises a CDR1 sequence consisting of the amino acid sequence GIDFSIYW (SEQ ID NO: 1), a CDR2 sequence consisting of the amino acid sequence INSDSSTI (SEQ ID NO: 2), and a CDR3 sequence consisting of the amino acid sequence ARKNGGLDYAMDY (SEQ ID NO: 3), and
   (ii) a light chain variable region which comprises a CDR1 sequence consisting of the amino acid sequence KSISKY (SEQ ID NO: 4), a CDR2 sequence consisting of the amino acid sequence SGS, and a CDR3 sequence consisting of the amino acid sequence QQHNEYPWT (SEQ ID NO: 5),
   wherein the functional fragment is Fab, Fab', F (ab')$_2$, scFv, a diabody, a triabody, a tetrabody, or a minibody.

2. The antibody or the functional fragment thereof according to claim 1, wherein the antibody is derived from a mouse.

3. The antibody or the functional fragment thereof according to claim 1, wherein the antibody is IgG or IgM.

4. A polynucleotide encoding the antibody or the functional fragment thereof according to claim 1.

5. An expression vector comprising the polynucleotide according to claim 4.

6. A method for testing a possibility of having developed a cancer, the method comprising (1) a step of measuring an amount or a concentration of an antigen in a biological sample collected from a subject, using the antibody or the functional fragment thereof according to claim 1,
   wherein the antigen is 3'-sialyl lactose, and the cancer pancreatic cancer or melanoma.

7. The method according to claim 6, further comprising (2) a step of determining that the possibility of having developed the cancer in the subject is high, when a value of the amount or the concentration of the antigen measured in the step (1) is equal to or higher than a preset cutoff value.

8. A method for diagnosing a cancer in a subject, the method comprising:
   (1a) a step of measuring an amount or a concentration of an antigen in a biological sample collected from the subject, using the antibody or the functional fragment thereof according to claim 1; and
   (2a) a step of determining that the possibility of having developed the cancer in the subject is high, when a value of the amount or the concentration of the antigen measured in the step (1a) is equal to or higher than a preset cutoff value, wherein the antigen is 3'-sialyl lactose, and the cancer is pancreatic cancer or melanoma.

9. The method according to claim 8, further comprising (3) a step of applying a diagnostic method for the cancer to the subject for which the possibility of having developed the cancer is determined to be high in the step (2a).

10. The method according to claim 9, wherein the diagnostic method for the cancer applied in the step (3) is at least one method selected from the group consisting of a biopsy method, a PET test method, a CT test method, and an ultrasonic test method.

11. A method for testing and treating a cancer in a subject, the method comprising:
   (1b) a step of measuring an amount or a concentration of an antigen in a biological sample collected from the subject, using the antibody or the functional fragment thereof according to claim 1;
   (2b) a step of determining that the possibility of having developed the cancer in the subject is high, when a value of the amount or the concentration of the antigen measured in the step (1b) is equal to or higher than a preset cutoff value;
   (3b) a step of applying a diagnostic method for the cancer to the subject for which the possibility of having developed the cancer is determined to be high in the step (2b); and
   (4b) a step of performing treatment for the cancer on a subject for which the possibility of having developed the cancer is determined to be high in the step (2b) or a subject determined to have the cancer in the step (3b),
   wherein the antigen is 3'-sialyl lactose, and the cancer is pancreatic cancer or melanoma.

12. A method for diagnosing a cancer in a subject, the method comprising a step of administering the antibody or the functional fragment thereof according to claim 1 labeled with a diagnostic agent, to a subject in need of the diagnosis, wherein the cancer is pancreatic cancer or melanoma.

13. The method according to claim 12, wherein the diagnostic agent is a radioactive substance.

14. A method for treating a cancer in a subject, comprising a step of administering the antibody or the functional fragment thereof according to claim 1 to a subject in need of the treatment,
   wherein the cancer is pancreatic cancer.

15. The method according to claim 14, wherein the antibody or the functional fragment thereof is labeled with a therapeutic agent.

16. The method according to claim 15, wherein the therapeutic agent is an anticancer agent.

17. The method according to claim 15, wherein the therapeutic agent is a radioactive substance.

* * * * *

SEQUENCE LISTING

```
<160> NUMBER OF SEQ ID NOS: 14

<210> SEQ ID NO 1
<211> LENGTH: 8
<212> TYPE: PRT
<213> ORGANISM: Mus musculus

<400> SEQUENCE: 1

Gly Ile Asp Phe Ser Ile Tyr Trp
1               5
```

```
<210> SEQ ID NO 2
<211> LENGTH: 8
<212> TYPE: PRT
<213> ORGANISM: Mus musculus

<400> SEQUENCE: 2

Ile Asn Ser Asp Ser Ser Thr Ile
1               5

<210> SEQ ID NO 3
<211> LENGTH: 13
<212> TYPE: PRT
<213> ORGANISM: Mus musculus

<400> SEQUENCE: 3

Ala Arg Lys Asn Gly Gly Leu Asp Tyr Ala Met Asp Tyr
1               5                   10

<210> SEQ ID NO 4
<211> LENGTH: 6
<212> TYPE: PRT
<213> ORGANISM: Mus musculus

<400> SEQUENCE: 4

Lys Ser Ile Ser Lys Tyr
1               5

<210> SEQ ID NO 5
<211> LENGTH: 9
<212> TYPE: PRT
<213> ORGANISM: Mus musculus

<400> SEQUENCE: 5

Gln Gln His Asn Glu Tyr Pro Trp Thr
1               5

<210> SEQ ID NO 6
<211> LENGTH: 24
<212> TYPE: DNA
<213> ORGANISM: Mus musculus

<400> SEQUENCE: 6
ggaatcgatt ttagtatata ctgg                                          24

<210> SEQ ID NO 7
<211> LENGTH: 24
<212> TYPE: DNA
<213> ORGANISM: Mus musculus

<400> SEQUENCE: 7
attaattcag atagcagtac aata                                          24

<210> SEQ ID NO 8
<211> LENGTH: 39
<212> TYPE: DNA
<213> ORGANISM: Mus musculus

<400> SEQUENCE: 8
gcaagaaaga atgggggatt ggactatgct atggactac                          39

<210> SEQ ID NO 9
<211> LENGTH: 18
<212> TYPE: DNA
<213> ORGANISM: Mus musculus
```

```
<400> SEQUENCE: 9
aagagcatta gcaaatat                                                18

<210> SEQ ID NO 10
<211> LENGTH: 27
<212> TYPE: DNA
<213> ORGANISM: Mus musculus

<400> SEQUENCE: 10
caacagcata atgaataccc gtggacg                                      27

<210> SEQ ID NO 11
<211> LENGTH: 138
<212> TYPE: PRT
<213> ORGANISM: Mus musculus

<400> SEQUENCE: 11
```

Met Asp Phe Gly Leu Ile Phe Phe Ile Val Ala Leu Leu Lys Gly Val
1               5                   10                  15

Gln Cys Glu Val Lys Leu Leu Gln Ser Gly Gly Gly Leu Val Gln Pro
            20                  25                  30

Gly Gly Ser Leu Lys Leu Ser Cys Ala Ala Ser Gly Ile Asp Phe Ser
        35                  40                  45

Ile Tyr Trp Met Ser Trp Val Arg Arg Ala Pro Gly Lys Gly Leu Glu
    50                  55                  60

Trp Ile Gly Glu Ile Asn Ser Asp Ser Ser Thr Ile Asn Tyr Ala Pro
65                  70                  75                  80

Ser Leu Lys Asp Lys Phe Thr Ile Ser Arg Asp Asn Ala Lys Asn Thr
                85                  90                  95

Leu Tyr Leu Gln Met Ser Lys Val Arg Ser Glu Asp Thr Ala Leu Tyr
            100                 105                 110

Tyr Cys Ala Arg Lys Asn Gly Gly Leu Asp Tyr Ala Met Asp Tyr Trp
        115                 120                 125

Gly Gln Gly Thr Ser Val Thr Val Ser Ser
    130                 135

```
<210> SEQ ID NO 12
<211> LENGTH: 122
<212> TYPE: PRT
<213> ORGANISM: Mus musculus

<400> SEQUENCE: 12
```

Met Val Leu Ile Ser Leu Leu Phe Trp Ile Ser Gly Ala Gln Cys Asp
1               5                   10                  15

Val Gln Ile Thr Gln Ser Pro Ser Tyr Leu Ala Ala Ser Pro Gly Glu
            20                  25                  30

Thr Ile Thr Ile Asn Cys Arg Ser Ser Lys Ser Ile Ser Lys Tyr Leu
        35                  40                  45

Ala Trp Tyr Gln Glu Lys Pro Gly Lys Thr Asn Lys Leu Leu Ile Tyr
    50                  55                  60

Ser Gly Ser Thr Leu Gln Ser Gly Ile Pro Ser Arg Phe Ser Gly Ser
65                  70                  75                  80

Gly Ser Gly Thr Asp Phe Thr Leu Thr Ile Ser Ser Leu Glu Pro Glu
                85                  90                  95

Asp Phe Ala Met Tyr Tyr Cys Gln Gln His Asn Glu Tyr Pro Trp Thr
            100                 105                 110

```
Phe Gly Gly Gly Thr Lys Leu Glu Ile Lys
        115                 120

<210> SEQ ID NO 13
<211> LENGTH: 414
<212> TYPE: DNA
<213> ORGANISM: Mus musculus

<400> SEQUENCE: 13
atggattttg ggctgatttt ttttattgtt gctcttttaa aaggggtcca gtgtgaggtg       60
aagcttctcc agtctggagg tggcctggtg cagcctggag gatccctgaa actctcctgt      120
gcagcctcag gaatcgattt tagtatatac tggatgagtt gggttcggcg ggctccaggg      180
aaaggactag aatggattgg agaaattaat tcagatagca gtacaataaa ctatgcacca      240
tctctaaagg ataaattcac catctccaga gacaacgcca aaaatacgct gtacctgcaa      300
atgagcaaag tgagatctga ggacacagcc ctttattact gtgcaagaaa gaatggggga      360
ttggactatg ctatggacta ctggggtcaa ggaacctcag tcaccgtctc ctca            414

<210> SEQ ID NO 14
<211> LENGTH: 366
<212> TYPE: DNA
<213> ORGANISM: Mus musculus

<400> SEQUENCE: 14
atggttctca tatccttgct gttctggata tcaggtgccc agtgtgatgt ccagataacc       60
cagtctccat cttatcttgc tgcatctcct ggagaaacca ttactattaa ttgcaggtca      120
agtaagagca ttagcaaata tttagcctgg tatcaagaga aacctgggaa aactaataag      180
cttcttatct actctggatc cactttacaa tctggaattc catcaaggtt cagtggcagt      240
ggatctggta cagatttcac tctcaccatc agtagcctgg agcctgaaga ttttgcaatg      300
tattactgtc aacagcataa tgaatacccg tggacgttcg gtggaggcac caagctggaa      360
atcaag                                                                 366
```